(12) United States Patent
Cho et al.

(10) Patent No.: US 9,867,832 B2
(45) Date of Patent: Jan. 16, 2018

(54) PHARMACEUTICAL COMPOSITION FOR INHIBITING IMMUNE RESPONSE THROUGH INDUCING DIFFERENTIATION INTO REGULATOR T CELLS AND PROMOTING PROLIFERATION OF REGULATOR T CELLS

(71) Applicant: LG CHEM, LTD., Seoul (KR)

(72) Inventors: Seok Goo Cho, Seoul (KR); Na Youn Kim, Seoul (KR); Eun Jung Kim, Seoul (KR); Keon Il Im, Seoul (KR); Jung Yeon Lim, Seoul (KR); Eun Joo Jeon, Seoul (KR)

(73) Assignee: LG CHEM, LTD., Seoul (KR)

( * ) Notice: Subject to any disclaimer, the term of this patent is extended or adjusted under 35 U.S.C. 154(b) by 190 days.

(21) Appl. No.: 14/779,812

(22) PCT Filed: Mar. 25, 2014

(86) PCT No.: PCT/KR2014/002504
§ 371 (c)(1),
(2) Date: Sep. 24, 2015

(87) PCT Pub. No.: WO2014/157918
PCT Pub. Date: Oct. 2, 2014

(65) Prior Publication Data
US 2016/0051558 A1   Feb. 25, 2016

(30) Foreign Application Priority Data

Mar. 25, 2013  (KR) .................. 10-2013-0031660
Jul. 5, 2013    (KR) .................. 10-2013-0078785

(51) Int. Cl.
| | | |
|---|---|---|
| *A61K 31/427* | (2006.01) | |
| *A61K 31/445* | (2006.01) | |
| *A61K 31/5377* | (2006.01) | |
| *A61K 31/675* | (2006.01) | |
| *A61K 31/541* | (2006.01) | |
| *A61K 39/395* | (2006.01) | |
| *A61K 45/06* | (2006.01) | |
| *A61K 31/203* | (2006.01) | |
| *A61K 31/54* | (2006.01) | |
| *C07K 16/28* | (2006.01) | |
| *A61K 35/17* | (2015.01) | |
| *A61K 38/18* | (2006.01) | |
| *C12N 5/0783* | (2010.01) | |
| *A61K 35/12* | (2015.01) | |

(52) U.S. Cl.
CPC .......... *A61K 31/541* (2013.01); *A61K 31/203* (2013.01); *A61K 31/54* (2013.01); *A61K 35/17* (2013.01); *A61K 38/1841* (2013.01); *A61K 39/3955* (2013.01); *A61K 45/06* (2013.01); *C07K 16/2809* (2013.01); *C07K 16/2818* (2013.01); *C12N 5/0637* (2013.01); *A61K 2035/122* (2013.01); *C12N 2501/15* (2013.01); *C12N 2501/385* (2013.01); *C12N 2501/51* (2013.01); *C12N 2501/515* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 2005/0196395 A1* | 9/2005 | Weiner ............... | C07K 16/2809 424/144.1 |
| 2006/0115899 A1* | 6/2006 | Buckner ............ | A61K 39/0008 435/372 |
| 2007/0172447 A1* | 7/2007 | Sakurada ............. | A61K 31/203 424/85.1 |
| 2011/0195094 A1 | 8/2011 | Ying et al. | |
| 2012/0088760 A1 | 4/2012 | Kim et al. | |
| 2012/0270203 A1 | 10/2012 | Kim et al. | |
| 2014/0024618 A1 | 1/2014 | Kim et al. | |

FOREIGN PATENT DOCUMENTS

| | | | |
|---|---|---|---|
| EP | 1 632 491 A1 | 3/2006 | |
| KR | 10-2009-0018593 A | 2/2009 | |
| KR | 10-2009-067125 A | 6/2009 | |
| KR | 10-2009-0075638 A | 7/2009 | |
| KR | 10-2010-57030 A | 5/2010 | |
| KR | 10-2012-0095022 A | 8/2012 | |
| WO | WO 2009/025477 A1 | 2/2009 | |
| WO | WO 2009025478 A1 * | 2/2009 | .......... C07D 413/04 |
| WO | WO 2012/111997 A2 | 8/2012 | |

OTHER PUBLICATIONS

Hippen et al., "Clinical Perspectives for Regulatory T Cells in Transplantation Tolerance," Seminars in Immunology, vol. 23, No. 6, 2011, pp. 462-468.
International Search Report, issued in PCT/KR2014/002504, dated Jun. 26, 2014.
Itoh, M. et al, "Thymus and Autoimmunity: Production of CD25+CD4+ Naturally Anergic and Suppressive T Cells as a Key Function of the Thymus in Maintaining Immunologic Self-Tolerance," J Immunol, 1999, vol. 162, pp. 5317-5326.
Sakaguchi, S. et al, "Regulatory T Cells and Immune Tolerance," Cell, May 30, 2008, vol. 133, pp. 775-787.

(Continued)

*Primary Examiner* — Jeffrey S Lundgren
*Assistant Examiner* — Michael Schmitt
(74) *Attorney, Agent, or Firm* — Birch, Stewart, Kolasch & Birch, LLP

(57) ABSTRACT

The present invention relates to new medical use of (tetrahydropyran-4-yl)-[2-phenyl-5-(1,1-dioxo-thiomorpholine-4-yl)methyl-1H-indol-7-yl]amine, and more particularly, to a pharmaceutical composition containing the compound as an active ingredient, which is used for inhibiting an immune response, and/or for inducing differentiation into regulator T cells from undifferentiated T cells and/or promoting proliferation of regulator T cells.

10 Claims, 10 Drawing Sheets
(4 of 10 Drawing Sheet(s) Filed in Color)

(56) References Cited

OTHER PUBLICATIONS

Extended European Search Report for European Application No. 14776253.8, dated Nov. 11, 2016.
Morris et al., "Naturally-existing CD4+CD25+Foxp3+ regulatory T cells are required for tolerance to experimental autoimmune thyroiditis induced by either exogenous or endogenous autoantigen," Journal of Autoimmunity, vol. 33, No. 1, Aug. 2009, pp. 68-76.
Yang et al., China Journal of Leprosy and Skin Diseases, vol. 23, No. 9, pp. 797-799.
Zhou, Z., et al, Acta Biophysica Sinica, Feb. 2012, vol. 28, No. 2, pp. 93-111.

* cited by examiner

[Fig. 1]
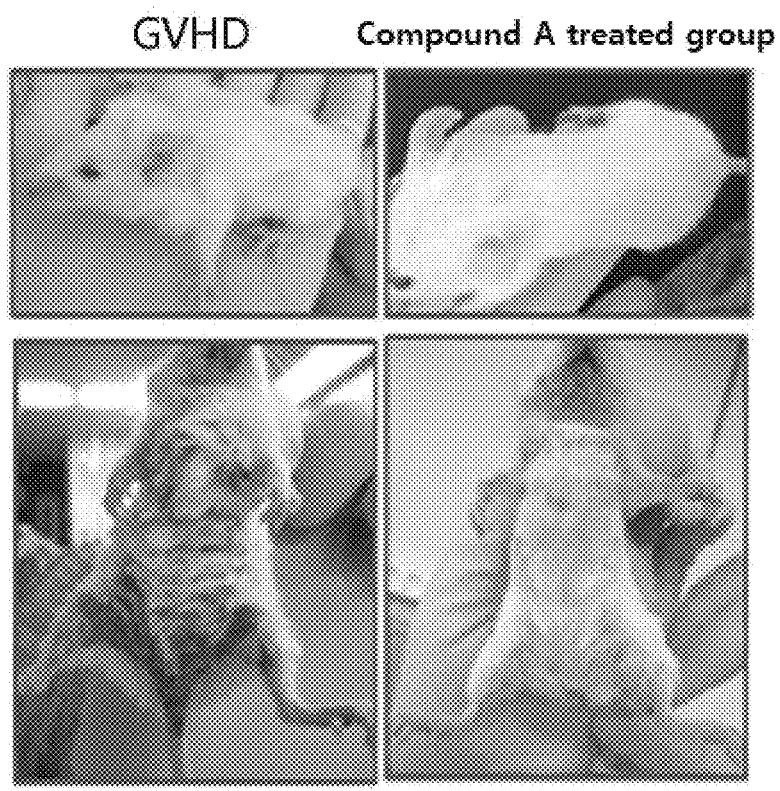

[Fig. 2]
(A)
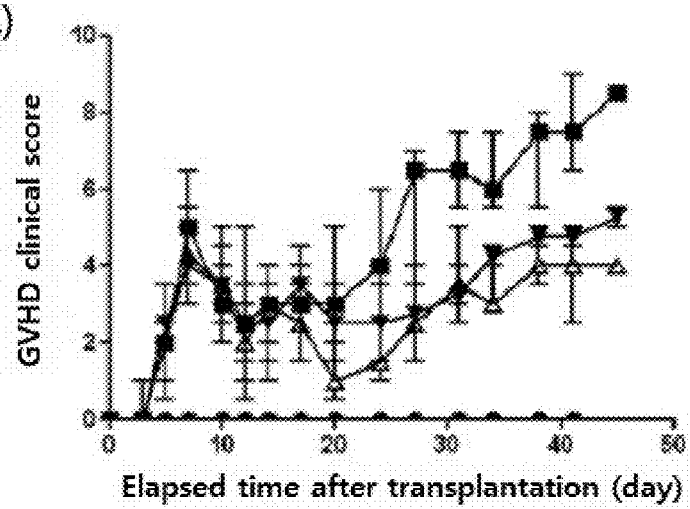
(B)
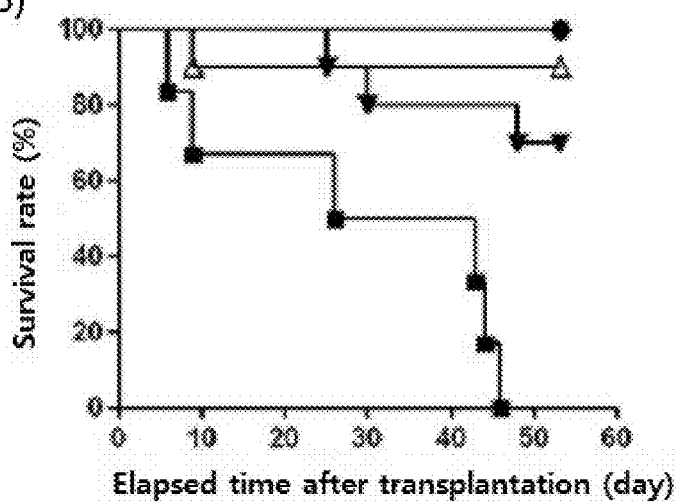
(C)
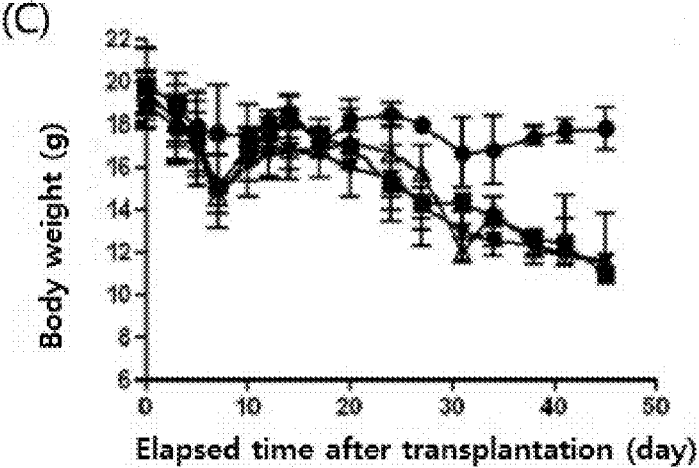

[Fig. 3]
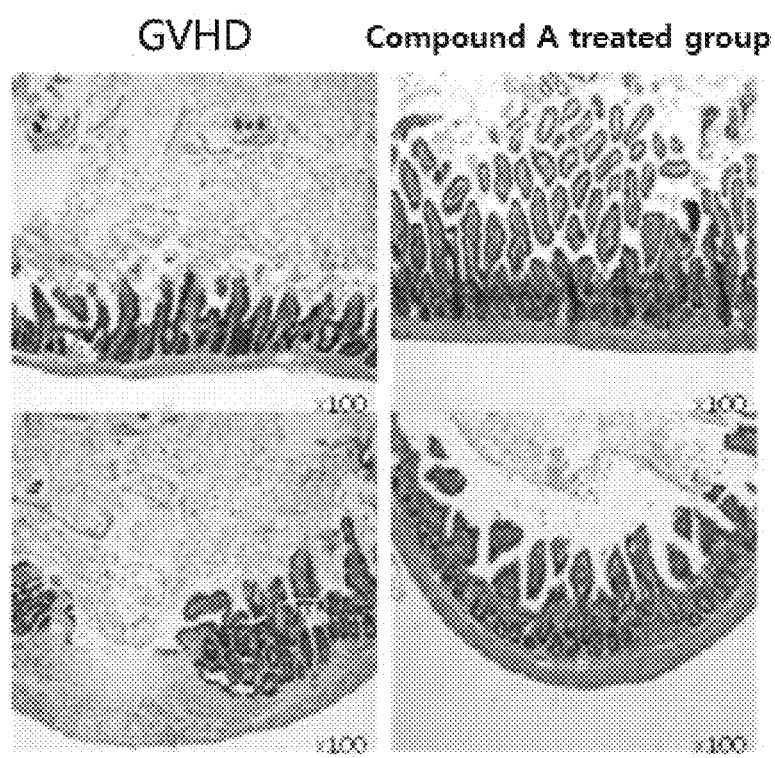

[Fig. 4]
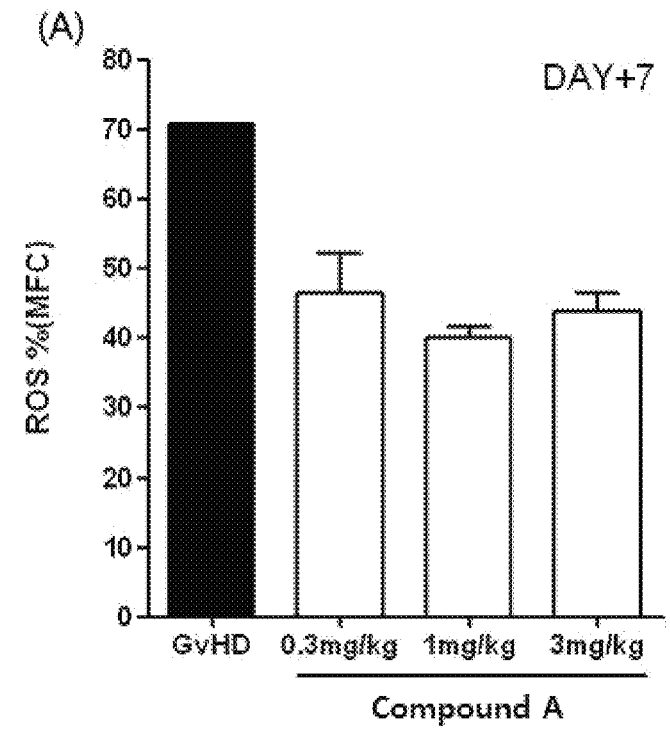
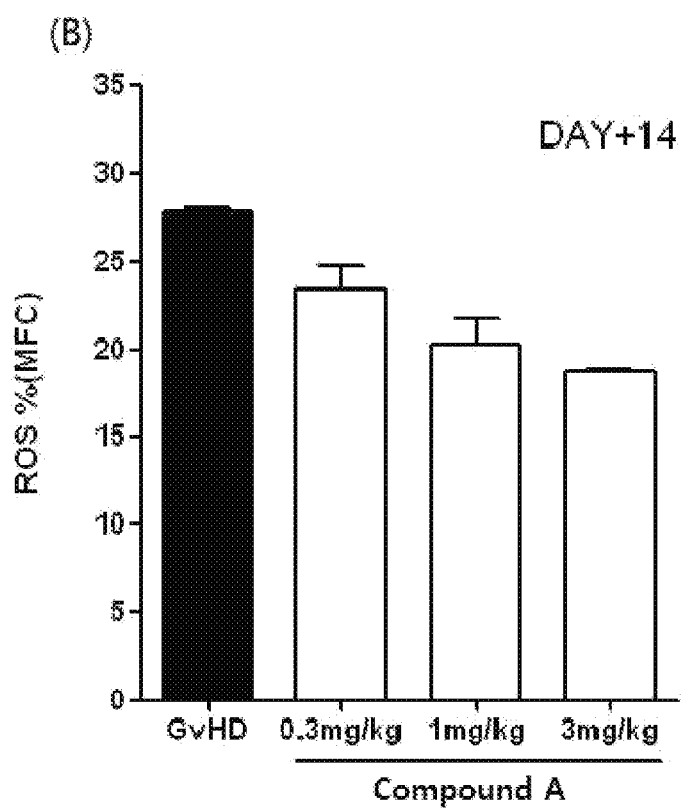

[Fig. 5]
(A)
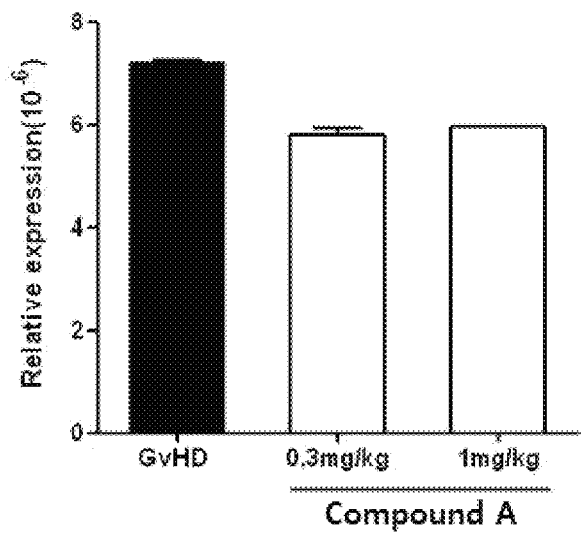
(B)
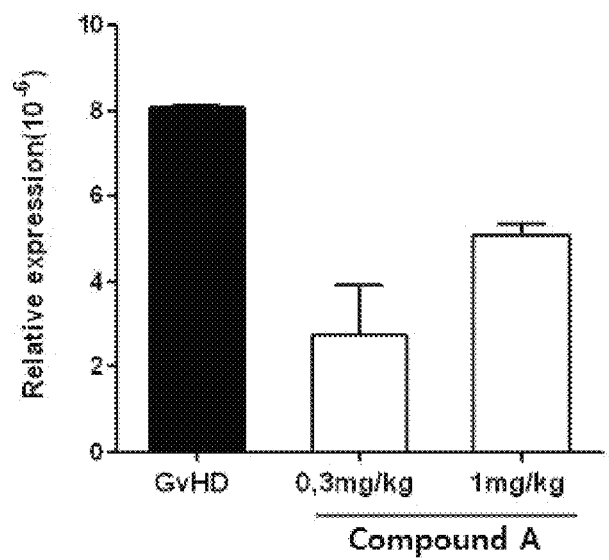

[Fig. 6]
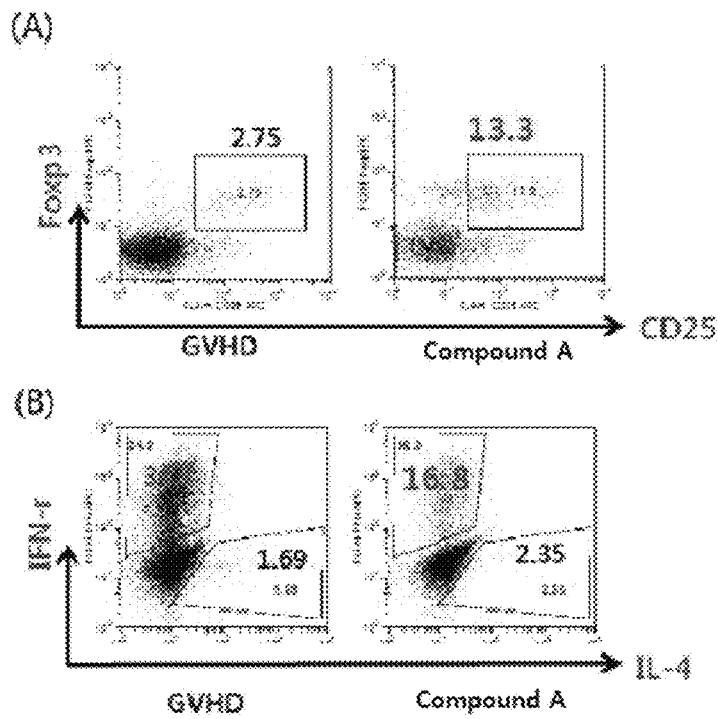
[Fig. 7]
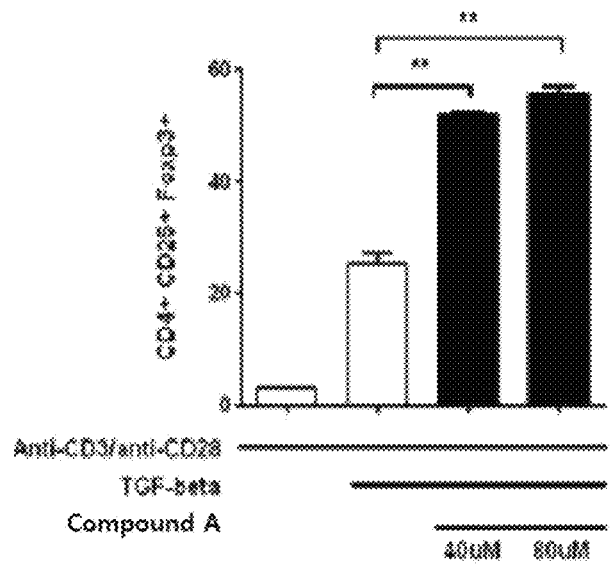

[Fig. 8]
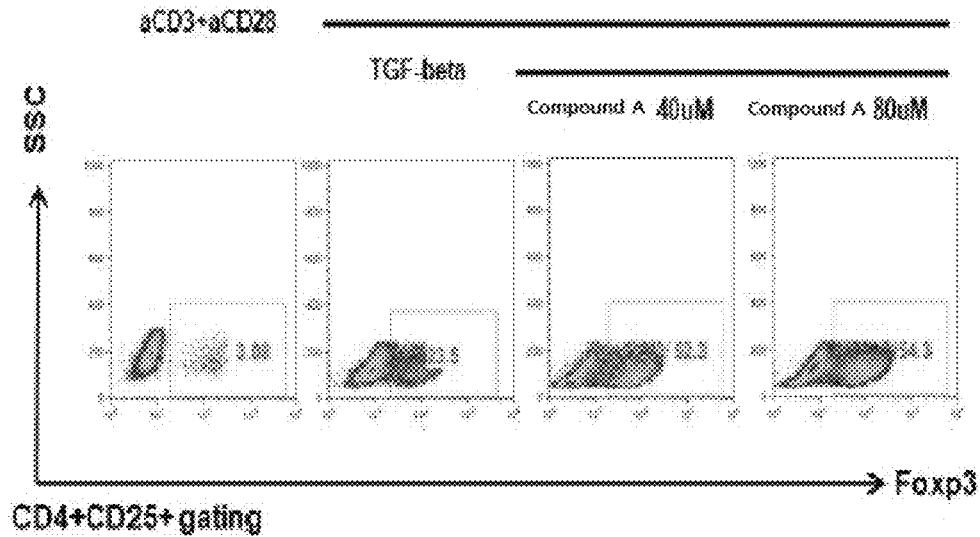
[Fig. 9]
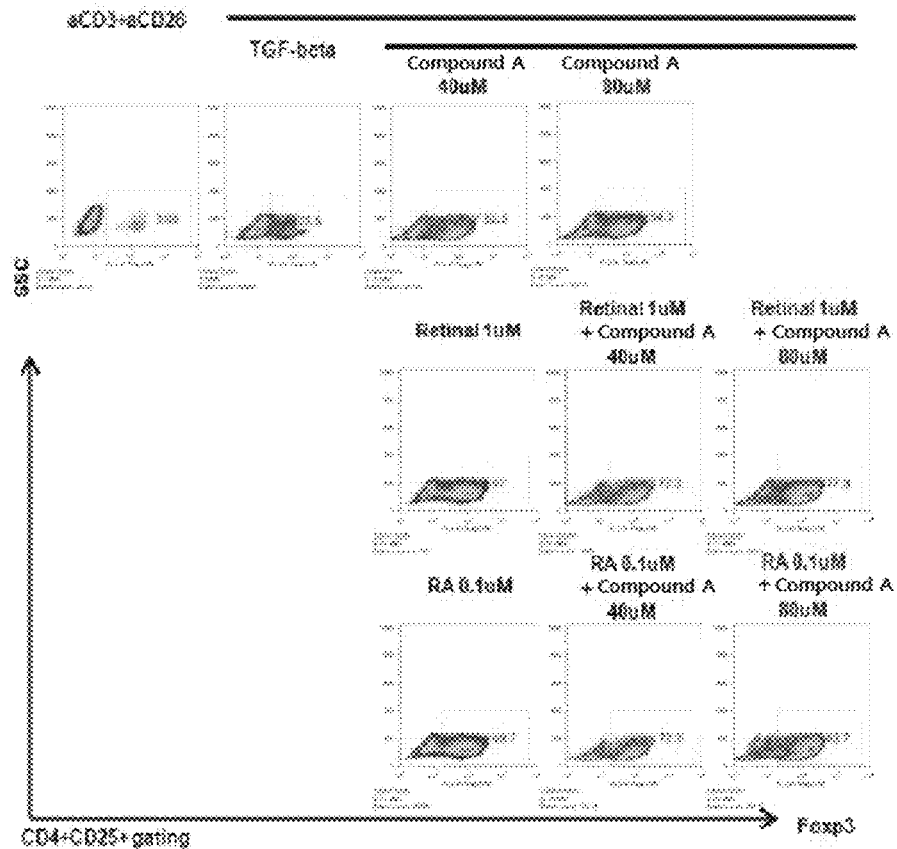

[Fig. 10]
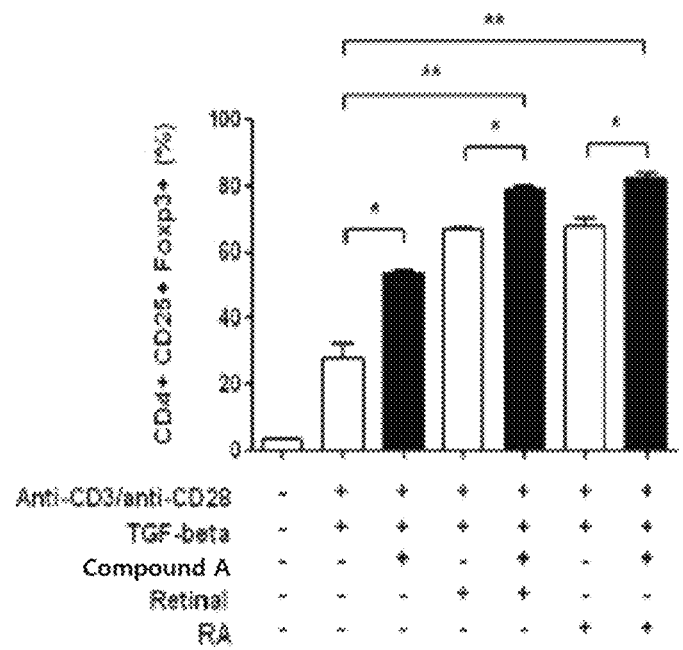
[Fig. 11]
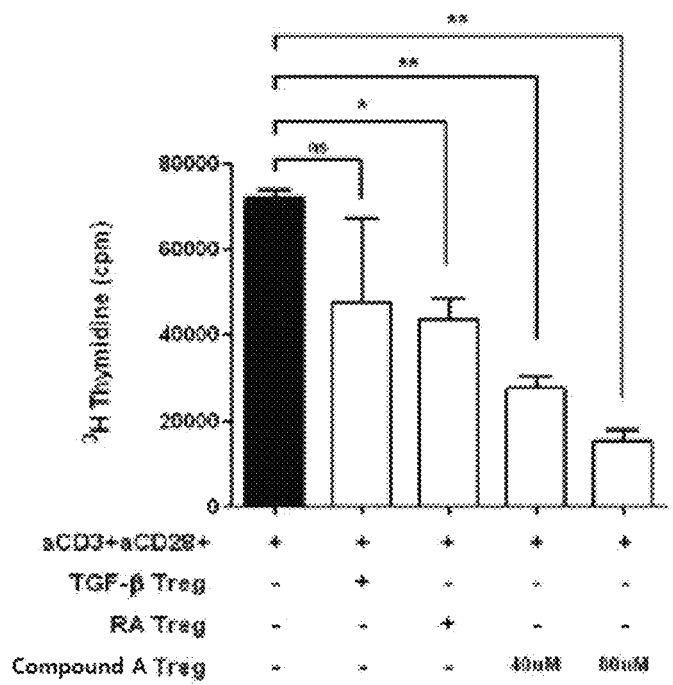

[Fig. 12]
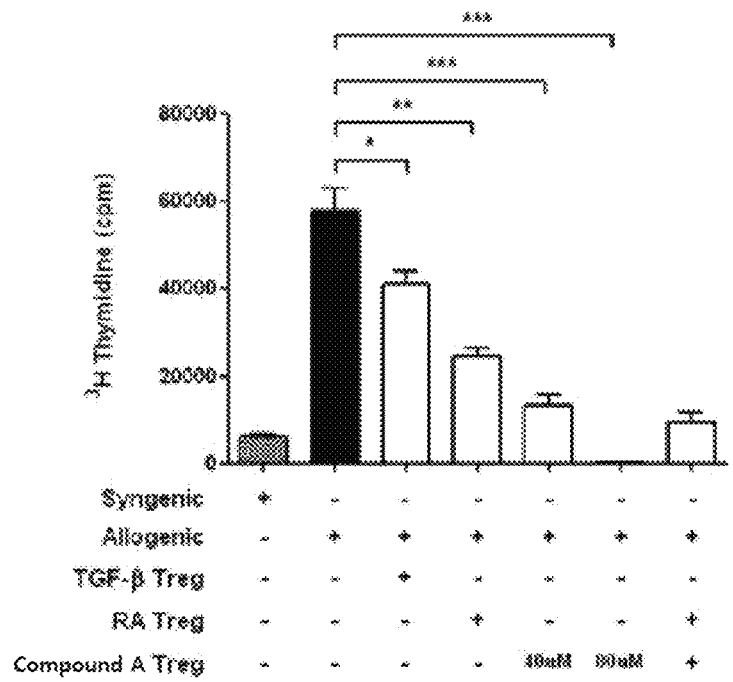
[Fig. 13]
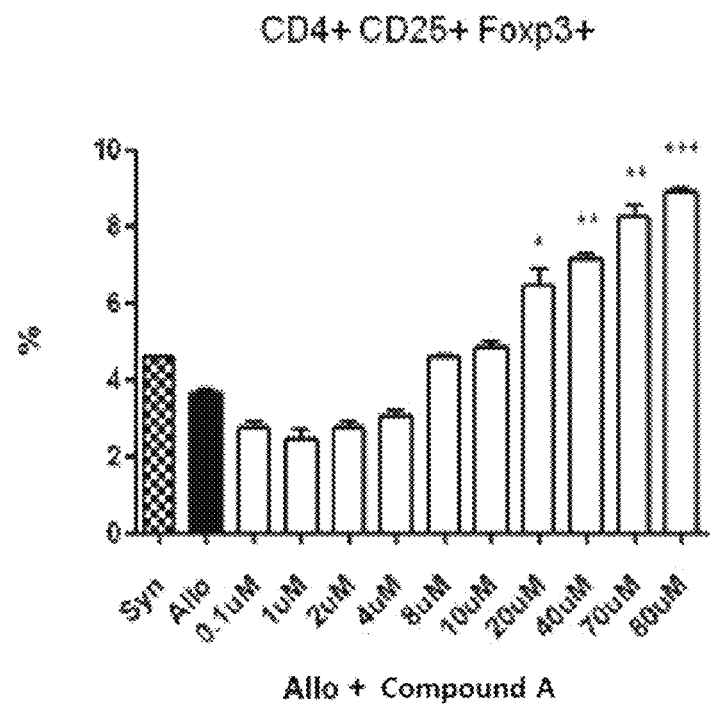

[Fig. 14]
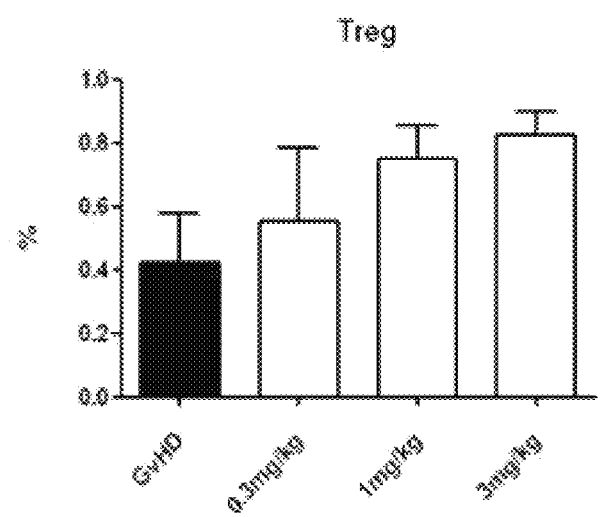

PHARMACEUTICAL COMPOSITION FOR INHIBITING IMMUNE RESPONSE THROUGH INDUCING DIFFERENTIATION INTO REGULATOR T CELLS AND PROMOTING PROLIFERATION OF REGULATOR T CELLS

TECHNICAL FIELD

The present invention relates to a novel medical use of (tetrahydropyran-4-yl)-[2-phenyl-5-(1,1-dioxo-thiomorpholin-4-yl)methyl-1H-indol-7-yl]amine. More specifically, the present invention relates to a method for the prevention or treatment of various immune diseases including graft-versus-host disease (GVHD) via the action of (tetrahydropyran-4-yl)-[2-phenyl-5-(1,1-dioxo-thiomorpholin-4-yl)methyl-1H-indol-7-yl]amine on inducing differentiation and promoting proliferation of regulatory T cells, and immune regulatory action of activated regulatory T cells; a pharmaceutical composition for use in such a method; and a method for obtaining regulatory T cells for use in the prevention or treatment of immune diseases by the use of the pharmaceutical composition.

BACKGROUND ART

Immunity refers to self-protective action from foreign substances by recognizing and removing foreign antigenic substances existing in the body. Immune response can be largely divided into cell-mediated immune response and humoral immune response. In humoral immune response, antibodies secreted by B cells recognize foreign antigens and neutralize them, help phagocytosis of macrophages by binding to the surface of other cells recognized as being non-self, or augment specific immune response by activating the complement system. In cell-mediated immune response, cytotoxic T cells (Tc cells) directly inactivate foreign antigens or activate macrophages by secreting cytokines such as IL-2 and IFN-gamma. As such, in immune response, the ability to discriminate between self and non-self antigen is absolutely important.

However, in a specific situation of transplantation of allogeneic or xenogeneic cells, tissues or organs, it is necessary to suppress immune response to prevent rejection of beneficial foreign graft. For example, to treat blood cancers such as leukemia, myeloma, lymphoma and aplastic anemia, allogeneic bone marrow transplant or hematopoietic stem cell transplant has been used as an effective treatment method. However, in the case of immune rejection response by recognizing a host as non-self antigen, the graft derived from a donor may cause damage to tissue, skin, organ and the like of a recipient, and even death in the worst case. As such, a disease in which a graft damages tissues of a host by causing immune rejection response is called graft-versus-host disease (GVHD). For example, in the case of stem cell transplant, it refers that new cells (graft) transplanted to bone marrow recognize the tissues of the patient (host) as foreign so that the stem cells of the allogeneic donor damage tissue, skin, digestive organ, or organ such as liver and the like of the recipient. In the pathogenesis of graft-versus-host disease, antigen-presenting cells of the patient activate T cells among transplanted bone marrow cells to differentiate into Th1 cells and increase the secretion of cytokines such as IL-2 and IFN-gamma, thereby activating cytotoxic T cells and natural killer cells, and they attack the organs of the patient to cause graft-versus-host disease. The major cause of graft-versus-host disease is allogeneic bone marrow transplant or hematopoietic stem cell transplant. Specifically, it has been reported that graft-versus-host disease is caused by hematopoietic stem cell transplant and 15-30% of the patients died. Therefore, to prevent occurrence of graft-versus-host disease and to ensure that graft survives for a long time, the immune system of the recipient that recognize foreign antigen should be evaded or the immune response should be suppressed.

In addition, in immune hypersensitivity reaction such as allergic reaction, in the case that the immunological reaction of a subject causes larger damage than invading foreign substances, suppression of immune reaction is necessary. Examples of such allergic diseases are allergic rhinitis, asthma, atopic dermatitis and the like. Furthermore, autoimmune diseases refer to a disease in which the immune system is to overly sensitive to the part of the subject's body so that the capacity of discriminating the self from the non-self is defective, destroying its own body. Autoimmune diseases also need treatment for suppressing immune response. Examples of such autoimmune diseases are rheumatic arthritis, insulin-dependent diabetes mellitus, multiple sclerosis, lupus, psoriasis, inflammatory bowel disease, ulcerative colitis, myasthenia gravis, polymyositis, dermatomyositis, autoimmune cytopenias, vasculitis syndrome, systemic lupus erythematosus and the like. All over the world, diseases caused by immune hypersensitivity reaction have been increased, but the root cause for such diseases has not been sufficiently investigated. Therefore, suppression of immune reaction has been widely used as a useful therapy for the treatment of patients suffering from immune diseases such as transplant rejection, graft-versus-host disease, allergic disease and autoimmune disease. At present, many chemical immunosuppressants for suppression of immune reaction have been developed, and cyclosporin A showed the best clinical effect and has been widely used for autoimmune diseases including graft-versus-host disease, transplant rejection and various inflammatory diseases. When cyclosporin A is used at high doses, it completely suppresses the activation of T cells to treat diseases, but has the disadvantage of showing considerable side effects including kidney toxicity. Therefore, it is recommended to use at low doses. In addition, to help overcome reduced medicinal effect due to low-dose use, administration in combination with 2 or 3 other immunosuppressants has been carried out. However, for co-administration, there is a prerequisite that the mechanism of action and the toxicity site of two compounds are different. Therefore, there is a need to develop more effective immunosuppressant which can replace conventional immunosuppressants.

Meanwhile, T cells—one of the cell groups that play a central role in the immune system—mature in the thymus and are classified into CD4-positive helper T cell (Th cell) and CD8-positive cytotoxic T cell. Via a series of differentiation procedures, helper T cells differentiate into T cells having intrinsic properties—Th1 (T helper type 1), Th2 (T helper type 2), Th17 (T helper type 17), regulatory T cell (Treg cell) and the like. Regulatory T cell has a property of controlling inflammatory reaction by suppressing the function of abnormally activated immune cells, so that it has been known that immune diseases can be treated by the action of increasing activity of regulatory T cell. Regulatory T cell uses $CD4^+CD25^+$ as a marker and expresses transcription factor Foxp3. The importance of regulatory T cell in immune tolerance and autoimmune diseases is evident in scurfy mouse which has Foxp3 mutation. Scurfy mouse having Foxp3 mutation dies only a month after birth due to excessive activation of $CD4^+$ T cells and excessive production of inflammatory cytokines (Sakaguchi S. et al., Cell 2008, 133:775-787), and in humans it is the cause of Foxp3 gene mutation hereditary disease, IPEX (immunodysregulation polyendocrinopathy enteropathy X-linked syndrome) which causes many autoimmune diseases such as diabetes mellitus type 1, allergy, inflammatory bowel disease and the like (Itoh M. et al., J Immunol 1999, 162:5317-5326). Therefore, it can be expected that various immune diseases including autoimmune diseases and chronic inflammatory diseases can be treated by activating regulatory T cells or administering a medication having regulatory T cells as an active ingredient. However, regulatory T cells are differentiated cells having immunosuppressive function as compared with other T lymphocytes produced from the thymus, and they are already stimulated by self-antigen in the thymus. Regulatory T cells are comprised of about 5% of thymus T lymphocytes, and about 10-15% of $CD4^+$ T lymphocytes exist in the end-organ. As a result, it is very difficult to obtain a therapeutically effective amount of regulatory T cells, and a method for obtaining a large number of regulatory T cells effectively is desired.

Meanwhile, Korean Patent Application Publication No. 10-2009-0018593 provides novel indole or indazole compounds having activity of inhibiting cellular necrosis and a therapeutic agent for the treatment of necrosis-associated diseases comprising thereof. However, the above patent document discloses the activity of the above indole or indazole compounds on inhibiting cellular necrosis and association with some necrosis-associated diseases such as hepatic disease, neurodegenerative disease and the like only, and never mentions an association of the above compounds with regulatory T cells, the efficacy on suppressing immune response or the possibility of being used in the treatment of immune hypersensitivity reaction-associated diseases.

Accordingly, the present inventors sought to provide compounds having excellent immunosuppressive efficacy which can replace or assist conventional immunosuppressants. As a result, the present inventors found that the compounds of Korean Patent Application Publication No. 10-2009-0018593, specifically (tetrahydropyran-4-yl)-[2-phenyl-5-(1,1-dioxo-thiomorpholin-4-yl)methyl-1H-indol-7-yl]amine—which is known as a cellular necrosis inhibitor promotes differentiation from immature T cells into regulatory T cells and proliferation and shows excellent immunosuppressive efficacy, and thus can be widely applied to the treatment of transplant rejection, graft-versus-host disease, allergic diseases, autoimmune diseases and the like to accomplish the present invention.

DISCLOSURE OF INVENTION

Technical Problem

Accordingly, an object of the present invention is the provision of a pharmaceutical composition for suppressing immune response, comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

Another object of the present invention is the provision of a pharmaceutical composition for the prevention and treatment of immune disease such as transplant rejection, graft-versus-host disease, allergic disease, autoimmune disease and inflammatory disease, comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

Still another object of the present invention is the provision of a composition for inducing differentiation from immature T cell into regulatory T cell and/or promoting proliferation of regulatory T cell, comprising (tetrahydropyran-4-yl)-[2-phenyl-5-(1,1-dioxo-thiomorpholin-4-yl) methyl-1H-indol-7-yl]amine, a pharmaceutically acceptable salt or isomer thereof.

Still another object of the present invention is the provision of a method for obtaining regulatory T cell via induction of differentiation into regulatory T cell and promotion of proliferation, which comprises a step of treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

Still another object of the present invention is the provision of a pharmaceutical composition for prevention or treatment of immune disease such as transplant rejection, graft-versus-host disease, allergic disease, autoimmune disease and inflammatory disease, comprising regulatory T cell obtained by treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

Solution to Problem

To accomplish the above object, the present invention provides a pharmaceutical composition for use in suppressing immune response via the activation of regulatory T cell by inducing differentiation into regulatory T cell and/or promoting proliferation, comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

As one aspect, the present invention provides a pharmaceutical composition for suppressing immune response, comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

As another aspect, the present invention provides a pharmaceutical composition for the prevention or treatment of immune disease such as transplant rejection, graft-versus-host disease, allergic disease, autoimmune disease and inflammatory disease by suppressing immune response via the activation of regulatory T cell, comprising (tetrahydropyran-4-yl)-[2-phenyl-5-(1,1-dioxo-thiomorpholin-4-yl) methyl-1H-indol-7-yl]amine, a pharmaceutically acceptable salt or isomer thereof.

As still another aspect, the present invention provides a composition for inducing differentiation from immature T cell into regulatory T cell and/or promoting proliferation of regulatory T cell, comprising (tetrahydropyran-4-yl)-[2-phenyl-5-(1,1-dioxo-thiomorpholin-4-yl)methyl-1H-indol-7-yl] amine, a pharmaceutically acceptable salt or isomer thereof.

As still another aspect, the present invention provides a method for obtaining regulatory T cell via induction of differentiation into regulatory T cell and promotion of proliferation, which comprises a step of treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

As still another aspect, the present invention provides a pharmaceutical composition for prevention and treatment of immune disease such as transplant rejection, graft-versus-host disease, allergic disease, autoimmune disease and inflammatory disease, comprising regulatory T cell obtained by treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof.

The method for preparing the compound of the present invention, (tetrahydropyran-4-yl)-[2-phenyl-5-(1,1-dioxo-thiomorpholin-4-yl)methyl-1H-indol-7-yl]amine, may refer to the method disclosed in Korean Patent Application Publication No. 10-2009-0018593. The above patent document is herein incorporated by reference in its entirety.

The compound (tetrahydropyran-4-yl)-[2-phenyl-5-(1,1-dioxo-thiomorpholin-4-yl)methyl-1H-indol-7-yl]amine according to the present invention may form a pharmaceutically acceptable salt. Such a "pharmaceutically acceptable salt" includes non-toxic acid addition salt containing pharmaceutically acceptable anion—for example, a salt with inorganic acids such as sulfuric acid, hydrochloric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. In addition, a pharmaceutically acceptable base addition salt—for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. is also included. The compound (tetrahydropyran-4-yl)-[2-phenyl-5-(1,1-dioxo-thiomorpholin-4-yl)methyl-1H-indol-7-yl]amine according to the present invention may be converted to their salts by any of the conventional methods, and the salt formation could be easily carried out by a person skilled in the art without additional explanations thereon.

The term "isomer" in the present specification means those having the same chemical or molecular formula as, but optically or sterically different from, the compound, or salts thereof. The compound (tetrahydropyran-4-yl)-[2-phenyl-5-(1,1-dioxo-thiomorpholin-4-yl)methyl-1H-indol-7-yl]amine according to the present invention may have an asymmetric carbon center(s) in the structure, and so may exist in the form of optical isomer (R or S isomer), racemate, mixture of diastereomers, or individual diastereomer, etc. All the isomers and their mixtures are also covered by the present invention.

Hereinafter, the compound (tetrahydropyran-4-yl)-[2-phenyl-5-(1,1-dioxo-thiomorpholin-4-yl)methyl-1H-indol-7-yl]amine according to the present invention includes pharmaceutically acceptable salts and isomers thereof, unless otherwise explained.

The present invention is characterized in the provision of a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof for use in suppressing immune response.

In the present specification, the term "immunosuppression" or "immune response suppression" refers to the suppression of disadvantageous immune response to the body caused by a foreign or self-antigen.

The compound (tetrahydropyran-4-yl)-[2-phenyl-5-(1,1-dioxo-thiomorpholin-4-yl)methyl-1H-indol-7-yl]amine of the present invention can be used in suppressing immune rejection response which may occur in the transplantation of all cells, tissues and organs. For example, it can be used in suppressing immune rejection response at the time of transplanting skin, blood, cornea, liver, lung, intestine, pancreas, heart, kidney, bone marrow, stem cell, precursor cell, etc., and preferably can be used in suppressing immune rejection response caused by skin graft, bone marrow transplantation, stem cell transplantation, blood transfusion and organ transplantation.

Accordingly, a pharmaceutical composition of the present invention is useful in the treatment and prevention of transplant rejection and/or graft-versus-host disease by suppressing immune response to the transplanted organ, tissue or cell.

In the present specification, "treatment" means interrupting or delaying the progress of the disease when applied to a subject showing the onset of disease symptoms, and "prevention" means interrupting or delaying the sign of the onset of disease when applied to a subject who does not show, but is at risk of, the onset of disease symptoms.

In addition, a pharmaceutical composition of the present invention is useful in the treatment and prevention of various immune hypersensitivity—associated diseases caused by immune hypersensitivity reaction, preferably allergic diseases, autoimmune diseases and inflammatory diseases. Examples of the allergic diseases are allergic rhinitis, asthma, atopic dermatitis and the like. In addition, examples of the autoimmune diseases are rheumatic arthritis, insulin-dependent diabetes mellitus, multiple sclerosis, lupus, psoriasis, inflammatory bowel disease, ulcerative colitis, myasthenia gravis, polymyositis, dermatomyositis, autoimmune cytopenias, vasculitis syndrome, systemic lupus erythematosus and the like.

In the specific example of the present invention, to ascertain the effect of the compound (tetrahydropyran-4-yl)-[2-phenyl-5-(1,1-dioxo-thiomorpholin-4-yl)methyl-1H-indol-7-yl]amine of the present invention on suppressing immune response, an allogeneic immune response mouse model was prepared by transplanting bone marrow and spleen cells of the donor mouse to the radiation-irradiated recipient mouse, and the compound (tetrahydropyran-4-yl)-[2-phenyl-5-(1,1-dioxo-thiomorpholin-4-yl)methyl-1H-indol-7-yl]amine of the present invention was administered to measure whether immune transplant rejection occurs. As a result, the survival rate of the group in which the compound (tetrahydropyran-4-yl)-[2-phenyl-5-(1,1-dioxo-thiomorpholin-4-yl)methyl-1H-indol-7-yl]amine of the present invention is treated was considerably increased as compared with the non-treated group, and significant results were observed in evaluation of body weight and graft-versus-host reaction (FIGS. 1 and 2). In histological observation, as a result of H&E staining of large intestine, it was observed that villi and mucous membrane of the large intestine are destroyed in the disease mouse model in which the compound of the present invention was not treated, but the group in which the compound of the present invention was treated is similar to normal large intestine (FIG. 3).

In addition, as a result of observing immune response by oxidative stress in allogeneic immune response mouse model, it was observed that in the group in which the compound of the present invention was treated the generation ratio of reactive oxygen species (ROS) in cells was significantly suppressed in a dose- and time-dependent manner (FIG. 4), and the expression of high-mobility group protein B1 (hereinafter referred to as "HMGB1"), which is a marker for immune regulatory function, was significantly suppressed (FIG. 5), as compared with the group in which the compound of the present invention was not treated.

As such, in allogeneic immune response mouse model it was confirmed that the compound (tetrahydropyran-4-yl)-[2-phenyl-5-(1,1-dioxo-thiomorpholin-4-yl)methyl-1H-indol-7-yl]amine of the present invention decreases immune transplant rejection and suppresses the production of ROS and HMGB1, and cellular necrosis in tissues. Furthermore, as a result of ascertaining the possibility of regulating immune response at the cellular level, in the group in which the compound of the present invention was treated CD4+ CD25+Foxp3+ immune regulatory cells (regulatory T cells) was increased 6 times or more and CD4+IL-4 cells were increased, but CD4+IFN-γ was decreased more than half, as compared with the group in which the compound of the present invention was not treated (FIG. 6). IFN-γ is a representative graft-versus-host disease-causing cytokine secreted by transplanted donor T cells, and it can be known that the compound (tetrahydropyran-4-yl)-[2-phenyl-5-(1,1-dioxo-thiomorpholin-4-yl)methyl-1H-indol-7-yl]amine of the present invention suppresses the activation of transplanted T cells by the up-regulation of regulatory T cells and IL-4.

From such experiment results, it can be confirmed that the compound (tetrahydropyran-4-yl)-[2-phenyl-5-(1,1-dioxo-thiomorpholin-4-yl)methyl-1H-indol-7-yl]amine of the present invention increases regulatory T cells, suppresses the activation of transplanted T cells via immunosuppressive action of the increased regulatory T cells, controls inflammatory reaction, and has efficacy in suppressing immune response by decreasing reactive oxygen species (ROS) in cells and the expression of HMGB1. Therefore, the compound of the present invention can be helpfully used as a pharmaceutical composition for suppressing immune response, and still more widely applied to the treatment of immune diseases such as transplant rejection, graft-versus-host disease, allergic disease, autoimmune disease, inflammatory disease and the like which need the suppression of immune response.

A pharmaceutical composition for immunosuppression comprising the compound (tetrahydropyran-4-yl)-[2-phenyl-5-(1,1-dioxo-thiomorpholin-4-yl)methyl-1H-indol-7-yl] amine of the present invention may be used in combination with other known immunosuppressants. Examples of combinable other immunosuppressants are, but are not limited to, cyclosporin A, rapamycin, tacrolimus, sacrolimus, methotrexate, azathioprine, mycophenolate mofetil and various steroid preparations.

As still another aspect of the present invention, a pharmaceutical composition for inducing differentiation from immature T cell into regulatory T cell and/or promoting proliferation of regulatory T cell, comprising (tetrahydropyran-4-yl)[2-phenyl-5-(1,1-dioxo-thiomorpholin-4-yl) methyl-1H-indol-7-yl]amine, a pharmaceutically acceptable salt or isomer thereof is provided.

In the present specification, the term "regulatory T cell" refers to a cell which can regulate T cell response, uses CD4+CD25+ as a marker and expresses transcription factor Foxp3. The regulatory T cell has a property of controlling inflammatory reaction by suppressing the function of abnormally activated immune cells, and suppresses chronic inflammatory reaction so that effect on the treatment of immune tolerance and autoimmune diseases can be shown. Specifically, it is known that Foxp3 factor plays an important role in the differentiation and activation of regulatory T cell. Therefore, regulatory T cell induced by the compound (tetrahydropyran-4-yl)-[2-phenyl-5-(1,1-dioxo-thiomorpholin-4-yl)methyl-1H-indol-7-yl]amine of the present invention can be used in suppressing immune rejection response which may occur in the transplantation of all cells, tissues and organs. For example, it can be used in suppressing immune rejection response at the time of transplanting skin, blood, cornea, liver, lung, intestine, pancreas, heart, kidney, bone marrow, stem cell, precursor cell, etc., and preferably can be used in suppressing immune rejection response caused by skin graft, bone marrow transplantation, stem cell transplantation, blood transfusion and organ transplantation. Accordingly, regulatory T cell induced by the compound of the present invention is useful in the treatment and prevention of transplant rejection or graft-versus-host disease by suppressing immune response to the transplanted organ, tissue or cell. In addition, regulatory T cell induced by the compound of the present invention is useful in the treatment and prevention of various immune hypersensitivity—associated diseases caused by immune hypersensitivity reaction, preferably allergic diseases, autoimmune diseases and inflammatory diseases. Example of autoimmune diseases are rheumatic arthritis, insulin-dependent diabetes mellitus, multiple sclerosis, lupus, psoriasis, inflammatory bowel disease, ulcerative colitis, myasthenia gravis, polymyositis, dermatomyositis, autoimmune cytopenias, vasculitis syndrome, systemic lupus erythematosus and the like.

In the specific example of the present invention, it was confirmed that the compound (tetrahydropyran-4-yl)-[2-phenyl-5-(1,1-dioxo-thiomorpholin-4-yl)methyl-1H-indol-7-yl]amine of the present invention promotes the differentiation from CD4 T cells isolated from spleen cells of mouse into regulatory T cells (FIGS. 7 and 8), and such an effect is excellent comparable with retinal or retinoic acid which was known as a differentiation inducer in the past. Still more, it was confirmed that in the case that the compound of the present invention is treated in combination with retinal or retinoic acid the effect on promoting differentiation into regulatory T cell is more increased (FIGS. 9 and 10). In addition, in in vitro experiment regulatory T cells induced by the treatment of the compound of the present invention showed the effect on suppressing proliferation of T cells and allogeneic immune response cells, and in in vivo graft-versus-host disease mouse model, its effect on immune regulatory function of regulatory T cells was confirmed (FIGS. 11 to 14).

Therefore, the compound of the present invention or a composition comprising thereof can be helpfully used in large-scale production or concentration of therapeutically effective amount of regulatory T cells for the treatment of immune disease and chronic inflammatory diseases by inducing differentiation from immature T cells into regulatory T cells and/or promoting the proliferation of regulatory T cells.

Preferably, a pharmaceutical composition for inducing differentiation from immature T cell into regulatory T cell and/or promoting proliferation of regulatory T cell, comprising the compound of the present invention may further comprise anti-CD3 antibody, anti-CD28 antibody and TGF-beta for differentiation into regulatory T cells, and may further comprise retinal or retinoic acid which is a conventional differentiation inducer to further improve the effect on promoting differentiation and proliferation.

Regulatory T cells differentiated by the compound of the present invention show the phenotype of $CD4^+$, $CD25^+$ and $Foxp3^+$, and have the function of regulating and suppressing immune response in allogeneic immune response cells and GVHD mouse.

Furthermore, the present invention provides a composition for the treatment of immune disease such as transplant rejection, graft-versus-host disease, allergic disease, autoimmune disease and inflammatory disease, comprising regulatory T cell obtained by treating immature T cell with the compound of the present invention or a composition comprising thereof.

A pharmaceutical composition of the present invention may comprise a pharmaceutically acceptable carrier, diluent, excipient or a combination thereof, if needed, together with the compounds of the present invention. A pharmaceutical composition facilitates the administration of the compound into a living organism. There are various techniques to administer the compound, and they include, but are not limited to, oral, injectable, aerosol, parenteral and topical administration.

In the present specification, a pharmaceutically acceptable carrier means a carrier or diluent which does not considerably stimulate a living organism and does not inhibit biological activities and properties of the compound to be administered. In addition, the additive may facilitate the preparation, compressibility, appearance and flavor of the formulation. For example, a stabilizer, a surfactant, a slip modifier, a solubilizing agent, a buffering agent, a sweetening agent, a base compound, an absorbent, a flavor enhancer, a binding agent, a suspending agent, a hardening agent, an anti-oxidant, a polishing agent, a fragrance ingredient, a flavoring agent, a pigment, a coating agent, a wetting agent, a moisture-adjusting agent, a filler, an antifoaming agent, a refreshing agent, a masticating agent, an antistatic agent, a coloring agent, a sugar coating agent, an isotonic agent, a softening agent, an emulsifying agent, a sticking agent, a thickening agent, a foaming agent, a pH-adjusting agent, an excipient, a dispersing agent, a disintegrating agent, a waterproof agent, an antiseptic agent, a preservative, a solubilizing aid, a solvent, a plasticizer, etc. may be added, if needed.

The dosage of the compound (tetrahydropyran-4-yl)-[2-phenyl-5-(1,1-dioxo-thiomorpholin-4-yl)methyl-1H-indol-7-yl]amine comprised in a pharmaceutical composition of the present invention depends on the prescription of a physician, taking into account such factors as body weight, sex, age, condition of health, and diet of the patient, specific nature of the disease, administration time of the agent, administration method, mixing ratio of agents, and severity of the disease, etc. However, the dosage needed for the treatment of an adult is typically from about 1.0 mg to 2,000 mg per day, depending on the intensity and frequency of the administration. When administered to an adult via intramuscular or intravenous route, total dosage typically ranging from about 1.0 mg to 300 mg per day will be sufficient when separately administered in a single dosage, but for some patients a higher daily dosage may be desirable.

Effects of Invention

A pharmaceutical composition of the present invention can be helpfully used as a pharmaceutical composition for suppressing immune response, and still more can be widely applied to the treatment of transplant rejection, graft-versus-host disease, allergic diseases, autoimmune diseases and the like. In addition, it can be helpfully used in obtaining a therapeutically effective amount of regulatory T cells for the treatment of immune disease and chronic inflammatory diseases on a large scale by promoting differentiation from immature T cells into regulatory T cells and proliferation, and regulatory T cells obtained according to the present invention can be widely applied to the treatment of transplant rejection, autoimmune disease such as graft-versus-host disease, chronic inflammatory disease and the like which need the suppression of immune response.

BRIEF DESCRIPTION OF DRAWINGS

The patent or application file contains at least one color drawing. Copies of this patent or patent application publication with color drawing will be provided by the USPTO upon request and payment of the necessary fee.

FIG. 1 is photographs of GVHD mouse in which the compound (tetrahydropyran-4-yl)-[2-phenyl-5-(1,1-dioxo-thiomorpholin-4-yl)methyl-1H-indol-7-yl]amine (hereinafter referred to as "Compound A") is not treated and GVHD mouse in which Compound A is treated.

FIG. 2 is graphs showing GVHD clinical score (A), survival rate (B) and body weight (C) according to elapsed day after transplantation of GVHD mouse model in which bone marrow and spleen cells of a donor mouse are transplanted into a irradiated recipient mouse. ■ represents a GVHD mouse prepared by bone marrow and spleen cells transplantation, ● represents a mouse in which GVHD is not induced by bone marrow transplantation and not spleen cells, Δ represents a GVHD mouse model in which 0.3 mg/kg of Compound A is administered, and ▼ represents a GVHD mouse model in which 1 mg/kg of Compound A is administered.

FIG. 3 is photographs showing the H&E staining results of each large intestine of Compound A non-treated GVHD mouse and Compound A treated GVHD mouse.

FIG. 4 is graphs showing the reactive oxygen species (ROS) generation ratio of Compound A non-treated GVHD mouse and GVHD mice in which Compound A is treated in each dose on the $7^{th}$ day (A) and $14^{th}$ day (B) after treatment.

FIG. 5 is graphs showing relative expression of HMGB1 of Compound A non-treated GVHD mouse and GVHD mice in which Compound A is treated in each dose on the $7^{th}$ day (A) and $14^{th}$ day (B) after treatment.

FIG. 6 is the results of flow cytometry analysis for regulatory T cells (CD4+CD25+Foxp3+) and CD4+IFN-γ cells of the spleens isolated from Compound A non-treated GVHD mouse and Compound A treated GVHD mouse.

FIG. 7 is a graph showing the degrees of differentiation into regulatory T cells (CD4+CD25+Foxp3+) of CD4+ cells isolated from mouse spleen cells in which anti-CD3 (aCD3) and anti-CD28 (aCD28) are treated, TGF-beta is additionally treated thereto, and 40 μM or 80 μM of Compound A is additionally treated thereto.

FIG. 8 is the results of flow cytometry analysis for the degree of Foxp3+ expression of differentiated cells which are CD4+ cells isolated from mouse spleen cells in which anti-CD3 and anti-CD28 are treated, TGF-beta is additionally treated thereto, and 40 μM or 80 μM of Compound A is additionally treated thereto.

FIG. 9 is the results of flow cytometry analysis for effect on the differentiation into regulatory T cells in each group. In the course of inducing differentiation into regulatory T cells by treating CD4+ cells isolated from mouse spleen with anti-CD3 and anti-CD28, or additional TGF-beta, the groups are divided into 40 μM of Compound A treated group, 80 μM of Compound A treated group, 0.1 μM of retinoic acid (hereinafter referred to as "RA") treated group, 1 μM of retinal treated group, 0.1 μM of RA and 40 μM of Compound A treated group, 0.1 μM of RA and 80 μM of Compound A treated group, 1 μM of retinal and 40 μM of Compound A treated group, and 1 μM of retinal and 80 μM of Compound A treated group.

FIG. 10 is a graph showing the degrees of differentiation into regulatory T cells (CD4+CD25+Foxp3+). In the course of inducing differentiation into regulatory T cells by treating CD4+ cells isolated from mouse spleen with anti-CD3, anti-CD28 and TGF-beta, the groups are divided into Compound A single-treated group, retinal single-treated group, RA single-treated group, Compound A and retinal co-treated group, and Compound A and RA co-treated group.

FIG. 11 is a graph showing the results of suppressive effect on T cell proliferation via [$^3$H]thymidine analysis for regulatory T cells induced by the addition of aCD3 and aCD28, regulatory T cells induced by the addition of aCD3, aCD28 and TGF-β (denoted as "TGF-beta Treg"), regulatory T cells induced by the addition of aCD3, aCD28, TGF-β and RA (denoted as "RA Treg"), regulatory T cells induced by the addition of aCD3, aCD28, TGF-β and 40 μM of Compound A, and regulatory T cells induced by the addition of aCD3, aCD28, TGF-β and 80 μM of Compound A (denoted as "Compound A Treg").

FIG. 12 is a graph showing the results of suppressive effect on allogeneic immune response cell proliferation via [$^3$H]thymidine analysis for regulatory T cells induced by the addition of aCD3 and aCD28, regulatory T cells induced by the addition of aCD3, aCD28 and TGF-β (denoted as "TGF-beta Treg"), regulatory T cells induced by the addition of aCD3, aCD28, TGF-β and RA (denoted as "RA Treg"), regulatory T cells induced by the addition of aCD3, aCD28, TGF-β and 40 μM of Compound A, and regulatory T cells induced by the addition of aCD3, aCD28, TGF-β and 80 μM of Compound A (denoted as "Compound A Treg").

FIG. 13 is a graph showing the results of comparative analysis for the effect on inducing differentiation into regulatory T cells according to the concentration of Compound A in allogeneic immune cells.

FIG. 14 is a graph showing the results of comparative analysis for the effect on promoting differentiation into regulatory T cells according to the concentration of Compound A in graft-versus-host disease (GVHD) mouse model.

MODE FOR THE INVENTION

Hereinafter, the present invention is explained in more detail with the following examples. However, the following examples are only intended to facilitate understanding of the present invention, and the protection scope of the present invention is not limited thereto.

Example 1: Establishment of Allogeneic Immune Response Mouse Model 6-8 week-old C57BL/6 (H-2kb) mouse and BALB/c (H-2kd) mouse which have different MHC class from each other were purchased from OrientBio Co., Ltd. After passing the regulation of the management committee of the Department of Laboratory Animal, The Catholic University of Korea, the mice were used under its care. A recipient mouse BALB/c (H-2kd) was irradiated with systemic radiation at 800 cGy. Within 24 hours, bone marrow 5×10$^6$ cells and spleen 5×10$^6$ cells isolated from a donor mouse C57BL/6 (H-2kd) were transplanted into the allogeneic recipient mouse intravenously to induce a graft-versus-host rejection reaction model. The bone marrow-transplanted mouse was observed and evaluation was made of the following: weight, pose, activity, hair condition and skin density with evaluation criteria on the total ten-point scale, two points per each item (Table 1).

TABLE 1

| Score | Weight | Pose | Activity | Hair condition | Skin density |
|---|---|---|---|---|---|
| 0 | <10% | Normal | Normal | Normal | Normal |
| 1 | >10% to <25% | Slightly bent | Little decrease | Slightly messed | Scaling of foot and tail |
| 2 | >25% | Seriously bent | Motionless without stimulus | Heavily messed | Evident skin peeling |

Example 2: Flow Cytometry (FACS Analysis)

Mice were divided into a GVHD group in which (tetrahydropyran-4-yl)-[2-phenyl-5-(1,1-dioxo-thiomorpholin-4-yl)methyl-1H-indol-7-yl]amine (LG Life Sciences Ltd., Daejeon, Korea, hereinafter referred to as "Compound A") was treated as a test group and a GVHD group in which Compound A was not treated as a control group. The spleens of each group were isolated and single-cell isolation was then carried out. The expression of CD4+CD25+Foxp3+, which is the phenotype of regulatory T cell, and CD4+IFN-γ cells and CD4+IL-4 cells were analyzed by the use of fluorescent monoclonal antibodies and a flow cytometer.

Example 3: Measurement of Reactive Oxygen Species (ROS)

Animals of each group were sacrificed, and their spleens were isolated. After single-cell isolation, the obtained cells were washed with phosphate-buffered saline (PBS) twice. The reaction with 3 μM carboxy-H2DCFDA reagent was carried out at 37° C. for 10 minutes. After washing with PBS, the analysis was carried out with a flow cytometer at 540 nm.

Example 4: RT-PCR

Total RNA was extracted from the cells by the use of TRIzol reagent. 1 μg of RNA was reacted with AMV reverse transcriptase and random hexamer at 45° C. for 1 hour to synthesize cDNA. Real-time PCR was carried out by the use of a mixture in which 1 μg of cDNA as a template, primer S, primer AS and distilled water were mixed, and SYBR Green. The PCR was carried out by the use of I-IMGB 1 (5'-GAT GGG CAA AGG AGA TCC TAA G-3' and 5'-TCA CTT TTT TGT CTC CCC TTT GGG-3') with the condition of 35 cycles of at 95° C. for 15 seconds, at 60° C. for 10 seconds and at 72° C. for 30 seconds. Fluorescent data were measured by the use of Rad CFX96 Real-Time System (Bio-Rad Laboratories).

Example 5: Immunocytochemistry

4 μm of serial sections were obtained from the paraffin-embedded tissue, treated with xylene three times to remove paraffin, and then hydrated stepwise in 95%, 90% and 70% ethanol. After removing endogenous peroxidase in 0.5% hydrogen peroxide, the specimen was treated with normal goat serum for 30 minutes and then reacted with primary antibody which was diluted with 3% bovine serum albumin (BSA) in PBS according to the manufacturer's instruction for 1 hour. After primary antibody reaction to the expressed proteins directed to genes showing the difference of expression in the above study, the specimen was washed with Tris-buffered saline (TBS) three times, reacted with 5 μg/ml biotinylated anti-mouse/anti-rabbit IgG diluted in 3% BSA for 30 minutes and washed with TBS three times. The specimen was kept in 3 μg/ml horseradish peroxidase streptoavidin for 30 minutes, color development was carried out by the use of DAB and hydrogen peroxide, and counter staining was carried out with Meyer's hematoxylin or 1% methyl green.

Results

1. Suppression of Immune Transplant Rejection in Mouse Model by the Compound (tetrahydropyran-4-yl)-[2-phenyl-5-(1,1-dioxo-thiomorpholin-4-yl)methyl-1H-indol-7-yl]amine of the Present Invention In the present invention, observation was made of the effect of the compound (tetrahydropyran-4-yl)-[2-phenyl-5-(1,1-dioxo-thiomorpholin-4-yl)methyl-1H-indol-7-yl]amine of the present invention on suppressing immune rejection response via GVHD mouse model. As a result, the survival rate of the group in which the compound of the present invention is treated was considerably increased as compared with the non-treated group, and significant results were observed in evaluation of body weight and graft-versus-host reaction (FIGS. 1 and 2). In histological observation, as a result of H&E staining of large intestine, it was observed that villi and mucous membrane of the large intestine were destroyed in the disease mouse model in which the compound of the present invention was not treated, but the group in which the compound of the present invention was treated is similar to normal large intestine (FIG. 3).

2. Regulation of Oxidative Stress by (tetrahydropyran-4-yl)-[2-phenyl-5-(1,1-dioxo-thiomorpholin-4-yl)methyl-1H-indol-7-yl]amine ROS plays a very important role in the regulation of cellular function in the body and contributes to defense action of immune cells in the immune system. In necrotic cells, ROS is generated by mitochondria, thereby oxidizing HMGB1. Eventually, immune tolerance is caused by oxidized HMGB1.

Accordingly, the present inventors observed immune response by oxidative stress via GVHD mouse model. As a result, it was observed that in the group in which the compound of the present invention was treated the generation ratio of reactive oxygen species in cells was significantly suppressed depending on a dose- and time-dependent manner, as compared with the control group (FIG. 4).

3. Suppression of HMGB1 Generation by (tetrahydropyran-4-yl)-[2-phenyl-5-(1,1-dioxo-thiomorpholin-4-yl)methyl-1H-indol-7-yl]amine It has been well known that the release of HMGB1 has a possibility of the function for regulating inflammation and immunity. Therefore, in this study the animals of the test group in which GVHD mouse model was treated with the compound of the present invention and the control model was sacrificed, RNA was extracted from spleen cells, and then cDNA was synthesized and a comparative study on the expression of HMGB1 was carried out by real-time PCR. As a result, it was confirmed that the release of HMGB1 in the group in which the compound of the present invention was treated was significantly suppressed in a time-dependent manner, as compared with the control group (FIG. 5).

4. Regulation of Immune Response by (tetrahydropyran-4-yl)-[2-phenyl-5-(1,1-dioxo-thiomorpholin-4-yl)methyl-1H-indol-7-yl]amine The present inventors found out that in GVHD mouse model, immune transplant rejection was decreased, the production of ROS and HMGB1, and cellular necrosis in tissues were suppressed by the compound of the present invention, so that they intended to observe the possibility of regulating immune response in immune disease animal model. Accordingly, mice of the test group in which the compound of the present invention was treated and the control group were sacrificed, their spleens were isolated, single-cell isolation was carried out, and the function of immune regulation was searched via flow cytometry. As a result, in the group in which the compound of the present invention was treated CD4+CD25+Foxp3+ immune regulatory cells (regulatory T cells) were increased 6 times or more, as compared with the control group. In addition, CD4+IL-4 cells were increased, and CD4+IFN-γ was decreased by more than half (FIG. 6). In GVHD model, after irradiation of high-dose radiation the transplanted T cells of the donor are activated and proliferated by antigen-presenting cells of the host to secrete IFN-γ which is known as a representative GVHD causing cytokine. The above experimentation results showed that the compound of the present invention suppressed IFN-γ by the up-regulation of regulatory T cells and IL-4. Therefore, it can be known that the compound of the present invention can suppress immune response by suppressing the activation of the transplanted T cells.

Example 6: Confirmation about Effect of Inducing Differentiation into Regulatory T Cells by (tetrahydropyran-4-yl)-[2-phenyl-5-(1,1-dioxo-thiomorpholin-4-yl)methyl-1H-indol-7-yl]amine in In Vitro Experimentation Experimentation for investigating the effect of the compound of the present invention on the differentiation of lymphocyte Th cells was carried out. $5 \times 10^5$ CD4+ T cells isolated from mouse spleen cells were dispensed into a 24-well plate coated with 1 μg/ml of anti-CD3 (aCD3), and then treated with 1 μg/ml of anti-CD8 (aCD28) and 5 ng/ml of TGF-beta to induce the differentiation into regulatory T cells for 3 days. Before the differentiation into regulatory T cells, the compound (tetrahydropyran-4-yl)-[2-phenyl-5-(1,1-dioxo-thiomorpholin-4-yl)methyl-1H-indol-7-yl]amine (hereinafter referred to as "Compound A") (LG Life Sciences Ltd., Daejeon, Korea) of the present invention was treated with the concentration of 40 μM and 80 μM. For flow cytometry, anti-mouse CD4 PerCP, CD25 APC and FoxP3 PE fluorescence-labeled antibodies were added thereto and reacted at 4° C. for 30 minutes. After washing with PBS, the measurement was carried out with a flow cytometer (FACSCalibur™)

As such, as a result of treating with Compound A after creating a differentiation environment of regulatory T cells by stimulating CD4+ T cells with aCD3, aCD28 and TGF-beta, the expression of Foxp3+ was nearly doubled by promoting differentiation into regulatory T cells, as compared with the control group in which Compound A was not treated, and differentiation into regulatory T cells was increased in a Compound A concentration-dependent manner. Specifically, it can be known that Compound A promotes differentiation into Foxp3+Treg cells by regulating TGF-beta signals (FIGS. 7 and 8).

Example 7: Comparison of Proliferating Regulatory T Cells by Conventional Differentiation Inducer Retinal/Retinoic Acid and Compound A, and Confirmation about Effect of Combination Therapy in In Vitro Experimentation It has been known that RA increases differentiation into Foxp3 Treg in the presence of TGF-beta. From the experimentation results of Example 6, it was confirmed that Compound A strongly increased the expression of Foxp3+ specifically, so the experimentation in which Compound A was compared with the effect of the conventionally known RA was performed.

In the course that $5 \times 10^5$ CD4+ T cells isolated from mouse spleen cells were dispensed into a 24-well plate coated with 1 μg/ml of anti-CD3 (aCD3), and then treated with 1 μg/ml of anti-CD8 (aCD28) and 5 ng/ml of TGF-beta to induce the differentiation into regulatory T cells for 3 days, the groups were divided into (1) 40 μM or 80 μM of Compound A single-treated group, (2) 0.1 μM of retinoic acid (RA) single-treated group, (3) 1 μM of retinal treated group, (4) 0.1 μM of RA and 40 μM or 80 μM of Compound A treated group, and (5) 1 μM of retinal and 40 μM or 80 μM of Compound A treated group, and the effect on the differentiation into regulatory T cells of each group was then compared.

As above, as a result of treating CD4+ cells with each compound alone or in combination in the presence of aCD3, aCD28 and TGF-beta, in the case of treating Compound A alone, the expression of Foxp3+ was increased to a similar extent to the case of treating retinal or RA. In addition, in the cases of treating Compound A in combination with RA or retinal, the expression of Foxp3+ was increased as compared with the groups in which each compound was treated alone. These results confirmed that Compound A promoted differentiation into regulatory T cells in the differentiation of Th cells (FIGS. 9 and 10).

Example 8: Confirmation about Effect of Regulatory T Cells Induced by Compound A on Suppressing Proliferation of Allogeneic Immune Response Cells To confirm the function of regulatory T cells induced by Compound A (hereinafter referred to as "iTreg"), it was evaluated whether iTreg cells could suppress T cell proliferation (aCD3+aCD28+ stimulation) and the activity of allogeneic immune response cells (allo response of B6 CD4+ and 2000 cGy B/c APC). For this, (1) Treg cells induced by the addition of aCD3 and aCD28, (2) Treg cells induced by the addition of aCD3, aCD28 and TGF-β (named as "TGF-beta Treg"), (3) Treg cells induced by the addition of aCD3, aCD28, TGF-β and RA (named as "RA Treg"), (4) Treg cells induced by the addition of aCD3, aCD28, TGF-β and 40 μM of Compound A (named as "Compound A Treg"), and (5) Treg cells induced by the addition of aCD3, aCD28, TGF-β and 80 μM of Compound A (named as "Compound A Treg"), and comparative analysis was carried out by a mixed-leukocyte culture test.

First, analysis for proliferation of T cells was carried out. $1 \times 10^5$ mouse CD4+ T cells were dispensed into a 96-well round bottom plate coated with 1 μg/ml of aCD3, and then stimulated with 1 μg/ml of anti-CD8 (aCD28) to create an environment for proliferation of CD4+ T cells.

Second, by the co-incubation of $1 \times 10^5$ donor spleen cells and $1 \times 10^5$ recipient spleen cells irradiated with radiation of 20 Gy, allogeneic immune response by donor spleen cells was induced to recipient spleen cells.

$1 \times 10^5$ regulatory T cells induced in vitro of 5 groups were added to each well in the ratio of 1:1 to CD4+ T cells and incubated at 37° C. for 3-4 days. Then, [$^3$H]thymidine was added thereto and incubated 8-14 hours before harvest. The radioactivity of the cells obtained by filtration with a Tomtec harvesting machine was measured.

From the experimentation results, it was confirmed that Treg induced by Compound A more efficiently suppressed the activity of T cells according to T cell proliferation and allogeneic immune response, as compared with TGF-beta Treg and RA Treg (FIGS. 11 and 12).

Example 9: Confirmation about Effect on Differentiation of Regulatory T Cells by Compound A in In Vitro Experimentation $1 \times 10^6$ CD4+ T cells isolated from the spleen cells of C57BL/6 and BALBc antigen-presenting cells (APCs) irradiated at 20 Gy were added to a 48-well plate and incubated at 37° C. for 5 days. The incubation was carried out under the condition that allogeneic immune response by antigen-presenting cells is induced to the spleen cells, and the treatment with Compound A at various concentrations before incubation was carried out for comparative analysis. The cells were harvested after 5-day incubation, and for flow cytometry anti-mouse CD4 PerCP, CD25 APC and FoxP3 PE fluorescence-labeled antibodies were added thereto and reacted at 4° C. for 30 minutes. After washing with PBS, the measurement was carried out with a flow cytometer (FACSCalibur™).

As a result, it was confirmed that regulatory T cells were increased according to the concentration of Compound A (FIG. 13).

Example 10: Confirmation about Effect on Increasing Regulatory T Cells by Compound A in In Vivo Graft-Versus-Host Disease (GVHD) Mouse Model 6-8 week-old C57BL/6 (H-2kb) mouse and BALB/c (H-2kd) mouse which have different MHC class from each other were used. A recipient mouse BALB/c (H-2kd) was irradiated with systemic radiation at 8 Gy. Within 24 hours, bone marrow $5 \times 10^6$ cells and spleen $5 \times 10^6$ cells isolated from a donor mouse C57BL/6 (H-2kd) were transplanted into the recipient mouse intravenously to induce graft-versus-host rejection reaction model (GVHD model). Compound A was intravenously injected into the GVHD model four times a week for two weeks. Mice were sacrificed, single-cell isolation was carried out, and the function of immune regulation in the spleen was investigated via flow cytometry. As a result, it was confirmed that in the group in which Compound A was administered CD4+CD25+Foxp3+ regulatory T cells were increased.

The invention claimed is:
1. A method for suppressing immune response, comprising
administering (tetrahydropyran-4-yl)-[2-phenyl-5-(1,1-dioxo-thiomorpholin-4-yl)methyl-1H-indol-7-yl] amine, a pharmaceutically acceptable salt or isomer thereof to a subject in need thereof.

2. The method according to claim 1, which is for suppressing immune rejection reaction to transplantation of skin, blood, cornea, liver, lung, intestine, pancreas, heart, kidney, bone marrow, stem cell or precursor cell.

3. The method according to claim 1, which is for the treatment and prevention of graft-versus-host disease, allergic disease, autoimmune disease or inflammatory disease.

4. A method for inducing differentiation into regulatory T cell, which comprises a step of
treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof ex vivo.

5. The method according to claim 4, wherein the composition further comprises an anti-CD3 antibody, an anti-CD28 antibody and TGF-beta.

6. The method according to claim 4, wherein the composition further comprises retinoic acid (RA) or retinal.

7. The method according to claim 4, wherein the regulatory T cell has the phenotype of $CD4^+$, $CD25^+$ and $Foxp3^+$.

8. A method for promoting proliferation of regulatory T cell, which comprises a step of
treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof ex vivo.

9. The method according to claim 8, wherein the composition further comprises retinoic acid (RA) or retinal.

10. A method for obtaining regulatory T cell via inducing differentiation and promoting proliferation of regulatory T cell, which comprises a step of
treating immature T cell with a composition comprising (tetrahydropyran-4-yl)-[2-phenyl-5-(1,1-dioxo-thiomorpholin-4-yl)methyl-1H-indol-7-yl]amine, a pharmaceutically acceptable salt or isomer thereof ex vivo.

* * * * *